US00PP29268P3

(12) United States Plant Patent
Korlipara

(10) Patent No.: US PP29,268 P3
(45) Date of Patent: May 1, 2018

(54) ***VERONICA* PLANT NAMED 'TNVERVB'**

(50) Latin Name: ***Veronica* hybrid**
Varietal Denomination: TNVERVB

(71) Applicant: Terra Nova Nurseries, Inc., Canby, OR (US)

(72) Inventor: Harini Korlipara, Canby, OR (US)

(73) Assignee: Terra Nova Nurseries, Inc., Canby ( * ) Notice: Subject to any disclaimer, the term of this patent is extended or adjusted under 35 U.S.C. 154(b) by 55 days.

(21) Appl. No.: 14/999,758

(22) Filed: Jun. 22, 2016

(65) Prior Publication Data

US 2017/0374779 P1 Dec. 28, 2017

(51) Int. Cl.
*A01H 5/02* (2018.01)

(52) U.S. Cl.
USPC ..... Plt./251
CPC ..... *A01H 5/02* (2013.01)

(58) Field of Classification Search
USPC ..... Plt./251
See application file for complete search history.

*Primary Examiner* — Anne Marie Grunberg
(74) *Attorney, Agent, or Firm* — Klarquist Sparkman, LLP

(57) ABSTRACT

A new and distinct form of *Veronica* plant characterized by purple blue flowers in narrow spikes, a dense, compact, spreading habit, small, medium green leaves, excellent branching with flower spikes at end of every branch, excellent vigor, and good garden performance.

1 Drawing Sheet

Botanical denomination: *Veronica* hybrid.
Variety designation: 'TNVERVB'.

BACKGROUND OF THE INVENTION

The present invention relates to a new and distinct cultivar of *Veronica*, given the name, 'TNVERVB'. *Veronica* is in the family Plantaginaceae (formerly Scrophulariaceae). This new cultivar was part of a planned breeding program for vigorous new *Veronica* using *Veronica* hybrid 'TNVERA' as the seed parent and an unknown *Veronica spicata* as the pollen parent.

Compared to the seed parent, *Veronica* hybrid 'TNVERA' (U.S. Plant Pat. No. 26,416), the new cultivar has a larger plant size, with purple blue flowers rather than warm pink.

Compared to *Veronica spicata* INSPIRE™ 'Blue', an unpatented plant, the new cultivar grows taller and wider and has darker purple blue flowers.

SUMMARY OF THE INVENTION

The following traits have been repeatedly observed and are determined to be the unique characteristics of 'TNVERVB'. The new cultivar exhibits the following characteristics:

1. purple blue flowers in narrow spikes,
2. a dense, compact, spreading habit,
3. small, medium green leaves,
4. excellent branching with flower spikes at end of every branch,
5. excellent vigor, and
6. good garden performance.

The new variety has been reproduced only by asexual propagation (stem cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the flowers of the new cultivar.

FIG. 2 shows three-year-old *Veronica* 'TNVERVB' growing full sun in a 5 gallon container in June in Canby, Oreg.

DETAILED PLANT DESCRIPTION

The following is a detailed description of the new *Veronica* cultivar based on observations of three-year-old specimens grown outside in the sun in 5 gallon containers in June in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, $5^{th}$ edition.

Plant:

*Form.*—Mat.

*Type.*—Evergreen, mat forming subshrub/perennial/small scale groundcover.

*Cold hardiness.*—USDA Zone 4-8.

*Size.*—Grows to 54 cm wide and 28 cm tall to the top of the foliage, 34 cm tall to the top of the flowers.

*Vigor.*—Excellent.

*Branching.*—Extremely well branched with about 300 stems from the crown, older stems branching freely, branches root into the ground as they spread.

*Non-flowering stem.*—Grow to 7 cm long and 1 to 1.5 mm wide, pubescent, internodes range from 0.2 cm to 17 mm long, young stems Yellow Green 147C; older woody stems grow to 3 mm wide, Brown 200A.

*Roots.*—Fibrous, freely branching, Greyed Orange 164D; plants root easily from divisions and stem tip cuttings (in about 10 to 14 days).

Leaf (on non-flowering stems):

*Type.*—Simple.

*Arrangement.*—Opposite.

*Number of leaves/stem.*—About 20.

*Blade size.*—Grow to 33 mm long and 16 mm wide.

*Shape.*—Lanceolate.

*Venation.*—Pinnate.

*Margins.*—Crenate.

*Apex.*—Acute.

*Base.*—Attenuate.

*Surface texture.*—Pubescent of both sides.

*Petiole description.*—To 18 mm long and 1 mm wide, pubescent, Yellow Green 147C.

*Leaf color.*—Top side Green N137A including main vein, bottom side Green 147B with main vein 147C.

Inflorescence:

*Type.*—Terminal raceme.

*Number of flowers.*—About 110 per raceme.

*Size of inflorescence.*—Spreads 2 cm wide and 10 cm long.

*Flowering stem.*—Grow to 19 cm long to base of inflorescence, Yellow Green 147C, pubescent; with leaves opposite, linear lanceolate, sessile, to 3 cm long near stem base and 7 mm wide, becoming smaller near top of stem, serrate, tip acute, base attenuate, pubescent on both sides, top side Green N137A including main vein, bottom side Green 147B with main vein 147C.

*Pedicel.*—1 mm long and 1 mm wide, pubescent, Yellow Green 147C.

*Bloom period.*—Middle of May to end of June in Canby, Oreg.

Flower bud:

*Size.*—6 mm long and 2 mm wide at the widest point prior to opening.

*Description.*—Convolute, narrowly oblong, apex obtuse.

*Surface texture.*—Glabrous.

*Color.*—Closest to Violet Blue 93B.

Flower:

*Type.*—Perfect.

*Shape.*—Zygomorphic.

*Corolla description.*—7 mm wide and 7 mm deep; both sides glabrous, tube 2 mm long and 1.3 mm wide, Violet Blue 93C inside and out, 4 lobes, 93B outside, 93C inside middle and 93B on inside edges, upper lobe broadly obovate, 3 mm long and 3 mm wide, tip obtuse, margin entire, side lobes ovate, 4 mm long and 2 mm wide, tip obtuse, margin undulate, bottom lobe reflexed 2 mm long and 1 mm wide, tip obtuse, margin entire.

*Calyx description.*—4-lobed, 3 mm wide and 2 mm deep, lobes linear, upper lobes 2.5 mm long and 1 mm wide, lower lobes 3 mm long and 1 mm wide, tips acute, margins entire, Green N137A and pubescent on both sides.

*Pistil description.*—1, exerted, 7.5 mm long, ovary round, 1 mm long and 1 mm wide, Yellow Green 144A, style 7 mm long, Violet Blue 93A, stigma Violet Blue N92A.

*Stamen description.*—2, filaments 5 mm long and Violet Blue 93B, anthers 1.5 mm long and Violet 86A, pollen White NN155A.

*Fragrance.*—None.

*Lastingness.*—A raceme blooms for about 3 weeks on the plant.

Fruit: An ovoid capsule. an ovoid capsule 2.5 mm long and 2 mm wide, glabrous, Brown 200A.

Seed: None seen.

Pests and diseases: The new cultivar is typical to the genus. No known resistances to pests or diseases. No problems have been found in Canby, Oreg.

I claim:

1. A new and distinct form of *Veronica* plant substantially as shown and described.

* * * * *

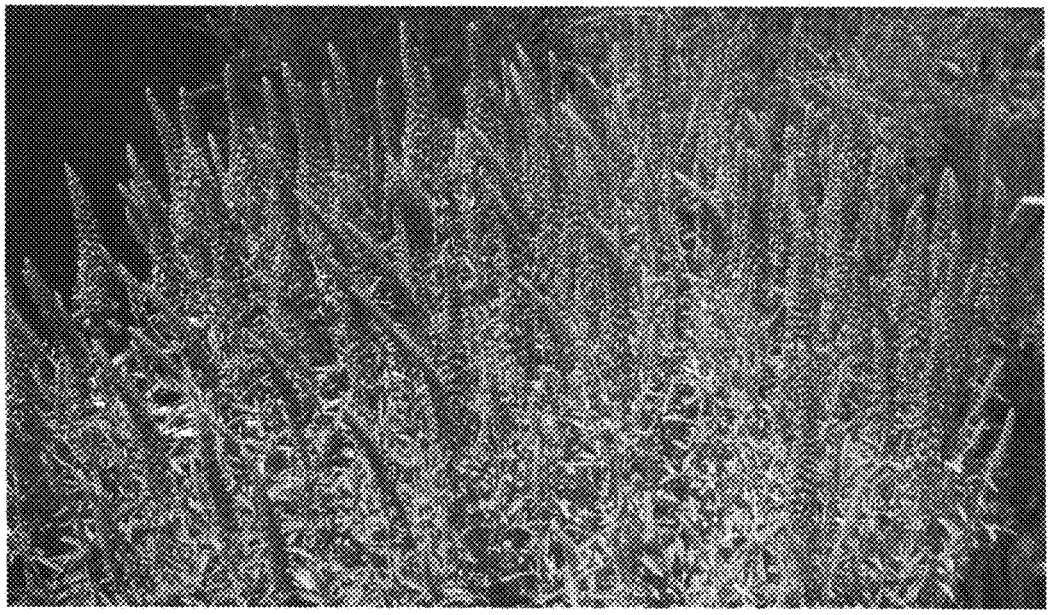

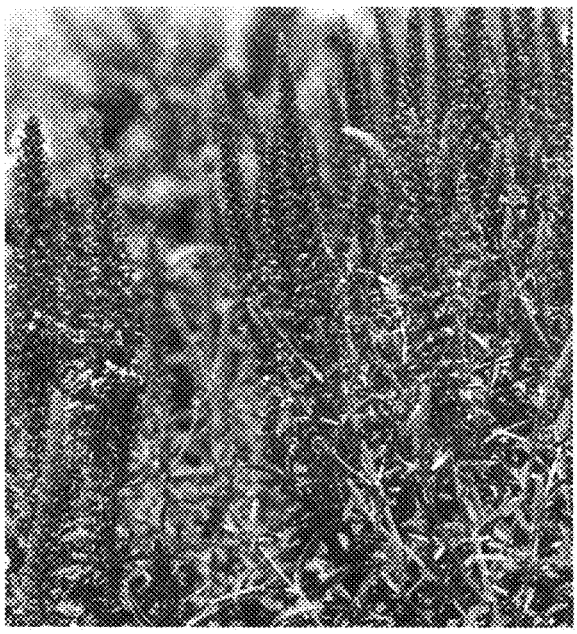
FIG. 1 on left,
FIG. 2 below